United States Patent
Pruche et al.

(10) Patent No.: US 7,211,043 B2
(45) Date of Patent: May 1, 2007

(54) METHOD, SYSTEM AND DEVICE FOR EVALUATING SKIN TYPE

(75) Inventors: Francis Pruche, Senlis (FR); Gilles Rubinstein, Paris (FR)

(73) Assignee: L' Oreal, Paris (FR)

( * ) Notice: Subject to any disclaimer, the term of this patent is extended or adjusted under 35 U.S.C. 154(b) by 69 days.

(21) Appl. No.: 10/289,344

(22) Filed: Nov. 7, 2002

(65) Prior Publication Data
US 2003/0108542 A1 Jun. 12, 2003

(30) Foreign Application Priority Data
Nov. 7, 2001 (FR) .................................. 01 14393

(51) Int. Cl.
*A61B 5/00* (2006.01)
(52) U.S. Cl. ..................................................... 600/306
(58) Field of Classification Search ................ 600/300, 600/301, 306, 309, 340, 362, 556–557; 424/9.1, 424/9.6, 9.8, 63, 401; 604/358, 362; 435/7.1, 435/405; 601/17
See application file for complete search history.

(56) References Cited

U.S. PATENT DOCUMENTS

| | | | | |
|---|---|---|---|---|
| 4,071,020 A | * | 1/1978 | Pugliese ..................... | 424/9.6 |
| 4,224,950 A | * | 9/1980 | Bore et al. .................. | 600/572 |
| 4,313,393 A | * | 2/1982 | Barbuscio et al. .......... | 116/200 |
| 4,401,122 A | * | 8/1983 | Clark, Jr. .................... | 600/358 |
| 4,430,013 A | * | 2/1984 | Kaufman .................... | 401/132 |
| 4,623,793 A | * | 11/1986 | Hofke et al. ............. | 250/341.2 |
| 4,894,547 A | * | 1/1990 | Leffell et al. ............ | 250/461.2 |
| 4,981,145 A | * | 1/1991 | Goldstein .................... | 600/573 |
| 5,018,531 A | * | 5/1991 | Hartman ..................... | 600/587 |
| 5,094,248 A | * | 3/1992 | Kawam ....................... | 600/572 |
| 5,140,986 A | * | 8/1992 | Klingner ..................... | 600/367 |
| 5,309,643 A | * | 5/1994 | McCollom .................. | 33/32.2 |
| 5,433,214 A | | 7/1995 | Brehm et al. | |
| 5,489,510 A | * | 2/1996 | Lopukhin et al. ............ | 435/7.1 |
| 5,938,593 A | * | 8/1999 | Ouellette .................... | 600/300 |
| 5,944,662 A | * | 8/1999 | Schoendorfer .............. | 600/362 |

(Continued)

FOREIGN PATENT DOCUMENTS

EP 0 399 856 11/1990

(Continued)

OTHER PUBLICATIONS

"Dimension". The American Heritage ® Dictionary of the English Language (2003). Retrieved May 20, 2005, from xreferplus. http://www.xreferplus.com/entry/4080831.*

(Continued)

*Primary Examiner*—Charles A. Marmor, II
(74) *Attorney, Agent, or Firm*—Oblon, Spivak, McClelland, Maier & Neustadt, P.C.

(57) ABSTRACT

A method, device and system for determining skin type. The method includes a step of applying at least one drop of substance onto a zone of the skin or on a collector member previously in contact with the zone of the skin. The substance can modify at least one physicochemical property of the surface of the zone or of the collector member exposed to the substance. After the drop has disappeared or been removed, the extent of the surface is evaluated and the skin type is determined as a function of this evaluation.

66 Claims, 4 Drawing Sheets

U.S. PATENT DOCUMENTS 6,251,070 B1 * 6/2001 Khazaka .................... 600/306
6,343,717 B1 * 2/2002 Zhang et al. ............... 222/209
6,524,242 B2 * 2/2003 Subramanyan et al. ..... 600/306

FOREIGN PATENT DOCUMENTS

| | | |
|---|---|---|
| FR | 1 333 761 | 8/1963 |
| FR | 2 001 768 | 10/1969 |
| JP | 2001-275993 | 10/2001 |

OTHER PUBLICATIONS

A. Mavon et al. (1997). Seburn and stratum corneum lipids Increase human skin surface free energy as determined from contact angle measurements: A study on two anatomical sites. *Elsevier Science: Colloids and Surfaces B: Biointerfaces 8*, 147-155.

* cited by examiner

FIG_1

FIG_2

FIG_3

FIG_4

FIG_5

FIG_6

FIG_7

FIG_8

FIG_9

FIG_14

FIG_10

FIG_11

FIG_13

FIG_12

FIG_15

FIG_16

FIG_17

FIG_18

FIG_19

FIG_20

METHOD, SYSTEM AND DEVICE FOR EVALUATING SKIN TYPE

CROSS REFERENCE TO RELATED APPLICATIONS

This application claims priority to French Application No. 01 14393, filed Nov. 7, 2001, the entire content of which is hereby incorporated by reference.

BACKGROUND OF THE INVENTION

1. Field of the Invention

The present invention relates to methods, systems and devices for determining skin types.

2. Description of the Background

Experience shows that consumers do not always select the best care products for their skin because they are not aware of their precise skin type and its specific needs. Consequently, there exists a need to enable determination of the skin type, for example, determination of whether the skin is dry or greasy. This determination can be used to evaluate the skin requirements for lipids and/or water. A better knowledge of the lipid and/or water requirements can help guide a formulator in making preparations that are targeted, or personalized.

U.S. Pat. Nos. 5,094,248 and 5,433,214 disclose devices for collecting sebum from the skin. Other devices are disclosed in the article "Sebum and stratum corneum lipids increase human skin surface free energy as determined from contact angle measurement: a study of two anatomical sites", published in *Colloid and Surface B: Biointerfaces,* 8 (1997), pp. 147–155. Such devices measure the contact angle between a drop deposited on the skin and the surface of the skin in order to show differences between the skin of the forehead and that of the forearm.

SUMMARY OF THE INVENTION

The invention seeks to further increase the diversity of methods and devices made available to the public and to professionals for determining skin types, and to make them sufficiently simple to enable use on a large scale.

In a first embodiment, the invention provides a method enabling a skin type to be determined, the method including a step of applying at least one drop of substance onto a zone of the skin or onto a sebum collector member previously put into contact with the zone of the skin. The substance is capable of modifying at least one physicochemical property of the surface of the zone or of the collector member exposed to the substance. After the drop has disappeared or been removed, the extent of the surface exposed to the substance is evaluated, e.g., by observing changes in appearance induced by the substance. The skin type is determined as a function of the extent.

The extent of the surface having its physicochemical property modified can be for example the size of a mark formed on the skin or on the collector. When the mark is circular in shape, the extent of the surface can be evaluated for example by measuring the diameter, the radius, the perimeter, or the area of the mark. The mark need not be circular so that lengths other than a diameter can be measured, such as an axis of an oval mark or other lengths characterizing the size of the mark. In other embodiments, quantities other than lengths are measured. In general, the extent can be evaluated by measuring a quantity characterizing the contact area between the drop and the skin or the collector member.

Such a method presents the advantage of being easy to implement while nevertheless obtaining information sufficiently precise to make diagnosis relatively easy.

In an aspect of the invention, the drop of substance is applied directly to the zone of the skin whose type is to be determined. In another aspect of the invention, the drop of substance is applied to a collector member previously placed into contact with the zone of the skin so as to transfer sebum onto the collector member. The collector member can optionally be a part of the human body.

The collector member can be, for example, a region of the arm, e.g., the forearm. Thus, in an implementation of the invention, the person whose skin type is to be determined can pass the forearm, for example, over the forehead, so that the sebum present on the surface of the forehead is transferred onto the forearm. The user can then apply a drop of substance on the forearm, where the sebum has been transferred. This procedure is advantageous, for example, when it is desired to avoid putting a drop of substance on the face. In addition, comparative evaluations can be performed, e.g., by comparing the results of a first evaluation on the collector member prior to transferring sebum and a second evaluation on the collector member after transfer. For example, an individual can compare the result of an evaluation performed on a forearm after it has been passed over the forehead, with the result of an evaluation performed on the individual's other forearm.

The collector member can also be a medium independent of the human body, for example, a sheet. For example, a sheet including cellulose fibers can form the collector member. Such a sheet can have graduations or a scale preprinted thereon.

In an embodiment of the invention, the substance is a colored substance or a substance which can color the skin. When the substance is a colored substance, its color can be obtained, for example, by incorporating one of the following coloring agents in a solvent, such as an aqueous solvent: Erythrosine B, carmine indigo, potassium permanganate, tannins, such as the oxidation products of polyphenols, melanines, henna, anthocyanes, fluorescent substances, in particular Dansyl chloride.

The substance can also present magnetic properties. For this purpose, the substance used can include, for example, magnetic particles, in particular particles containing iron, possibly associated with a polymer, a copolymer, or a plastics material, such as cellulose, polybutene, or polystyrene, for example.

The substance can also include at least one antibody, in particular an antibody specific to keratins. The antibody can be associated with at least one of the elements in the following list: magnetic particles, fluorescent compounds, enzymes (e.g., a peroxidase), a system of the "Elisa" type. The substance can also be capable of modifying the microrelief of the skin. The substance can have as its solvent: water, an alcohol, an oil, amongst others. The volume of a drop of substance deposited on the skin can lie, for example, in the range of 5 microliters (µl) to 100 µl, or in the range of 10 µl to 60 µl, or it may be equal to about 20 µl, for example.

In an embodiment of the invention, the drop is removed by an absorbent element, such as a strip of blotting paper or a cotton applicator bud, for example. Other means can be used without going beyond the scope of the present invention. For example, the drop can be removed by applying suction. It is also possible to allow the drop to disappear by evaporation, for example. Nevertheless, it may be preferable to remove the drop rather than to wait until it has evaporated.

The extent of the surface of the skin or of the collector member whose properties are modified by the drop of substance can be measured in numerous ways after the drop has disappeared or been removed, depending on the nature of the change that has taken place. This extent can be evaluated in situ, by measuring directly on the skin or on the collector member. In another embodiment, the area can be evaluated after transferring onto a medium a trace that has been left on the skin or on the collector member by the drop of substance.

For example, when using a drop of a substance that is colored or capable of coloring the skin or the collector member, the size of the mark left by the drop on the surface of the skin or of the collector member can be measured using various devices, including but not limited to a pair of dividers, a camera, a light ray, or an optionally graduated scale, possibly in association with an optical system.

When the contact between the drop of substance and the skin or the collector member leaves a trace that can be measured in non-optical manner, e.g., because of modifications to the microrelief or the electrical or magnetic properties of the skin or the collector member, it is possible, for example, to use at least one magnetic sensor or at least one non-optical sensor configured to deliver an image of the microrelief of the skin or of the collector member.

Where appropriate, the result of the measurement can be transmitted to a computer for analysis purposes. The results of the measurement may be entered into the computer via a keyboard or a touch-sensitive screen, for example. The result of the measurement can also be transmitted directly to the computer by the device used for taking the measurement, using a wire connection or a wireless connection. Where appropriate, the result of the measurement can be transmitted remotely over a computer network, such as the Internet, to a diagnosis center, for example.

By way of example, the drop of substance can be applied to various body locations including but not limited to the forehead, the top of the chest, the forearm, the top of the shoulder. Tests can be performed on different parts of the body and information useful for determining skin type can be obtained by comparing the results of the various tests.

It is also possible to apply different substances in succession to the skin or to the collector member. The different substances can present a variety of affinities with respect to lipids and/or water. Information useful for determining skin type can be obtained by comparing the results of the different tests. Thus, for example, it is possible to use in succession an aqueous substance and then an oily substance, or vice versa.

In an aspect of the invention, care treatment is recommended based on the information obtained as a result of the skin type evaluation.

In another of its embodiments, the invention provides a method of treating the skin, e.g., cosmetically. The method can include a step of applying at least one drop of a test substance on a zone of the skin or on a collector member previously in contact with the zone. The test substance is capable of modifying at least one physicochemical property of the surface of the zone of the skin or of the collector member exposed to the test substance. The substance can be colored or suitable for producing coloring on the zone of the skin or the collector member. After the drop has disappeared or been removed, the extent of the surface exposed to the test substance is evaluated. The type of the skin as a function of the extent can then be evaluated and the skin can be treated with a treatment substance, such as a cosmetic, as a function of the skin type.

To understand what is understood by "cosmetic" in the meaning of the present application, reference can be made to EEC Cosmetic Directive 76/768. The term "cosmetic treatment" covers any nontherapeutic treatment with a cosmetic as defined in the above Directive.

By way of example, the treatment can modify the affinity of the skin for the test substance, such that a new operation of determining skin type, after applying the care, can lead to a different result.

The region of the body or the face where the test is performed can be selected as a function of the kind of treatment which might be performed as a result of the test. Thus, the drop of test substance can be applied, for example, to the forearm when the treatment substance is intended for the entire body, and the drop of test substance can be applied to the forehead, for example, when the treatment substance is to be applied more particularly to the face.

The invention also provides a method of determining the effectiveness of a treatment, in particular a treatment for acting on the moisture and/or lipid content of the skin. The method includes the step of applying at least one drop of substance to a zone of the skin or to a collector member previously placed into contact with the zone. The substance can modify at least one physicochemical property of the surface of the zone of skin or of the collector member in contact with the drop. The extent of the surface of the zone of skin or of the collector member is evaluated after the drop has been removed or has disappeared by observing modifications induced by the substance. The treatment can be performed and the previous steps repeated on treated skin. The results before and after treatment are compared and an indication concerning the effectiveness of the treatment is deduced from the results.

In an aspect of the invention, when the extent of the surface of the skin or the collector member exposed to the substance corresponds to skin which is dryer than skin considered as being normal, the substance applied reduces skin dryness. When the extent of the surface corresponds to a skin which is greasier than a skin considered as being normal, the substance applied reduces the sebum content of the skin.

For example, if it is desired to evaluate the influence on the skin of a care product applied thereto, once a drop newly applied on the skin has been removed or has disappeared, it is possible to measure the extent of the surface exposed to the test substance, and to compare it with the surface exposed to the test product by the drop as applied initially. On the basis of the new measurement, it is thus possible to determine whether the care product is adequate.

In another of its embodiments, the invention provides a method of evaluating the physiological age of the skin, based on the fact that the lipid film of the skin tends to disappear with age. The method includes a step of applying at least one drop of substance onto a zone of the skin or onto a collector member previously put into contact with the zone. The substance modifies at least one physicochemical property of the surface of the zone of the skin or the collector member exposed to the substance. After the drop has disappeared or been removed, the extent of the surface of the zone of skin or of the collector member that has been in contact with the drop is evaluated by observing the modifications induced by the substance. The age of the skin is determined as a function of the extent.

The invention also provides an assembly including an applicator configured to apply a drop of a substance to the skin or to a collector member and at least one scale or measuring device for evaluating the extent of the surface of the skin or of the collector member that has been in contact with the drop, after the drop has disappeared or been removed. The scale can optionally be graduated. For example, the scale can carry markings configured to specify skin type directly.

When using a substance that is colored or that colors the skin, the scale can be associated with an optical system, e.g., enabling the scale to be viewed simultaneously with an enlarged image of the mark. The scale can also be carried by the applicator. The scale can also be a stick-on scale.

The scale can also be present on a medium onto which a trace left on the surface of the skin or the collector member by the drop of substance is to be transferred, after the drop has been removed or disappeared. In this case, the scale can be printed on such a medium, for example. The medium in question can be, for example, in the form of a reply card for mailing to a diagnosis center. The medium can also be a strip for inserting into a reader device, for example. The medium can have an adhesive face, intended to facilitate transfer onto the medium of the trace left by the drop of substance on the surface of the skin or the collector member.

The medium can be impregnated with a developer configured to react on coming into contact with the substance constituting the drop, so that during transfer onto the medium of the trace of substance left on the skin or the collector member, a reaction occurs on the medium, e.g., a coloring reaction.

Optionally, when the medium has an adhesive surface, it can enable particles of dead skin or other impurities present on the surface of the skin to be collected, and the diagnosis center can deliver information relating to skin type by comparing the information associated with the extent of the trace transferred onto the medium and information associated with the quantity of impurities deposited on the medium, in the zone of the adhesive surface that is situated around the transferred trace.

Where appropriate, the medium can include a protective sheet configured to cover the adhesive surface after the trace has been transferred. Such a protective sheet can present, for example, a surface treated so as to avoid adhering strongly to the adhesive surface.

The image of a mark formed on the medium by transfer can also be transmitted remotely to a diagnosis center, by fax or by means of a camera or a scanner.

The applicator can include a supply of substance and a portion that can be snapped off or that is designed to be cut or punctured.

The supply of substance can be formed in contact with at least one flexible wall. The supply of substance can be formed between two superposed sheets, for example.

By way of example, the applicator can include a duct through which the drop is delivered. The inside diameter of the duct can lie, for example, in the range 50 micrometers (μm) to 3 millimeters (mm), and preferably lying in the range approximately 0.1 mm to approximately 2 mm.

When a device for measuring the extent of the surface of the skin whose properties have been modified by the drop of test substance is used, the device can emit light rays towards the skin and pick up the reflected light. The light rays can be produced by at least one laser diode or by at least one light-emitting diode (LED), for example. Such light rays can make it possible, for example, to detect a modification to the reflective or color properties of the surface of the skin or of the collector member exposed to the drop of substance.

By way of example, the measuring device can also include at least one strip of sensors associated with an optical system enabling an image of a mark left on the skin or the collector member by the drop of substance to be projected onto the strip.

Where appropriate, the measuring device can include a lighting device for lighting the skin with light having spectral composition that is selected in such a manner as to excite fluorescence in a tracer. The measuring device can thus include, for example, an infrared or ultraviolet light source.

The measuring device can also include a camera, e.g., a camera connected to a personal computer. The measuring device can also include at least one magnetic sensor.

The measuring device can also include at least one non-optical sensor configured to deliver an image of microrelief on the skin or on the collector member. By way of example, the measuring device can also include an interface enabling data to be transmitted to a personal computer and/or to a computer network.

The invention also provides a device for measuring the extent of the surface of the skin or the collector member exposed to a drop of substance that modifies at least one physicochemical characteristic of the skin or of the collector member. The substance can be a colored substance or a substance that produces coloration on the skin or the collector member. The device includes a device for measuring the extent of the surface and a device for displaying a skin type as a function of the result of the measurement. By way of example, the device can deliver information in nonnumerical form of the type "dry skin", "normal skin", or "greasy skin", or in a variant it can deliver a numerical value, e.g., a score lying in the range n to m where n and m are integers, the digit n corresponding to skin that is very dry and the digit m to skin that is very greasy.

The invention also provides a scale having markings configured to indicate skin type directly. The invention also provides a medium onto which a trace left on the skin or the collector member by a drop of substance is to be transferred, the medium including marking configured to indicate skin type directly. The invention also provides a pair of dividers having markings configured to indicate skin type directly. The invention also provides a kit made up of an assembly including an applicator and a scale or a measuring device as defined above, together with a treatment substance for application to the skin, in particular a care product.

BRIEF DESCRIPTION OF THE DRAWINGS

A more complete appreciation of the invention and many of the attendant advantages thereof will be readily obtained as the same becomes better understood by reference to the following detailed description when considered in conjunction with the accompanying drawings, in which.

DESCRIPTION OF THE PREFERRED EMBODIMENTS

Throughout this text, including in the claims, the terms "including a" and "comprising a" should be understood as being synonymous with "including at least one" and "comprising at least one" respectively, unless otherwise specified.

Figure 1:
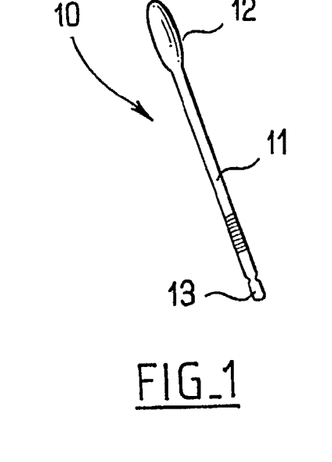
FIG. 1 is a diagram of an applicator configured to apply a drop of substance on the skin.
Figure 2:
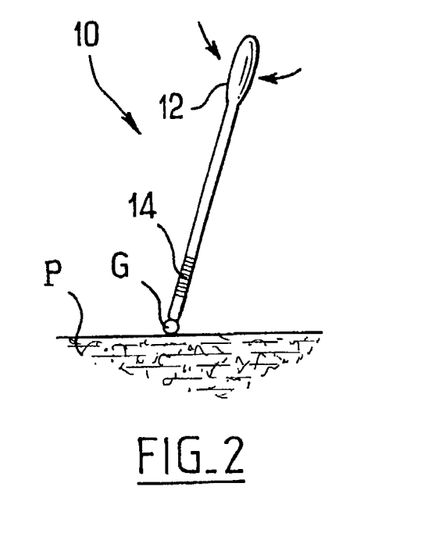
FIG. 2 shows a drop of substance being applied to the skin using the applicator shown in FIG. 1.

FIG. 1 shows an example of a device 10 for applying a drop G of colored substance onto the skin P. The device 10 is in the form of a pipette including a tube 11 communicating at one end with a supply 12 and provided at its other end with a breakable portion 13. The wall of the supply 12 can be deformable so as to enable the user to compress the supply and expel a drop of substance after the breakable portion 13 has been broken off, as shown in FIG. 2. The tube 11 can have graduations 14 configured to measure the size of a mark as explained below. The volume of the drop G suitable for placing on the skin can be, for example, in the range 5 μl to 100 μl, for example, about 20 μl.

Figure 3:
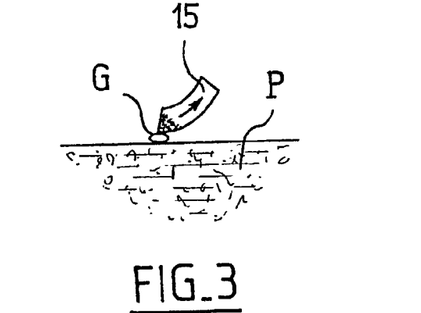
FIG. 3 shows the drop of substance being removed by a strip of absorbent paper.
Figure 4:
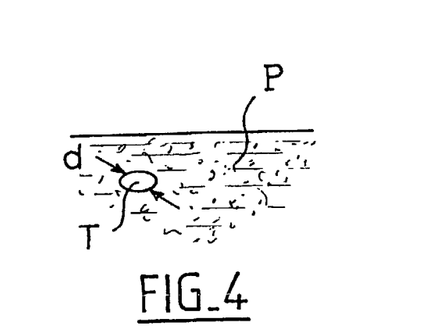
FIG. 4 is a diagram showing a mark left on the surface of the skin after the drop has been removed.

After applying a drop G of substance on the skin P, the drop is left there for a length of time sufficient to ensure that after the drop G is evaporated or removed, e.g., with a strip of blotting paper 15 as shown in FIG. 3, a mark T is formed due to contact between the substance and the skin. This mark T can be substantially circular and can present a diameter d, as shown in FIG. 4. The mark T can have other shapes, including ovals, and nonsymmetrical shapes depending on the properties of the surface of the skin.

Figure 5:
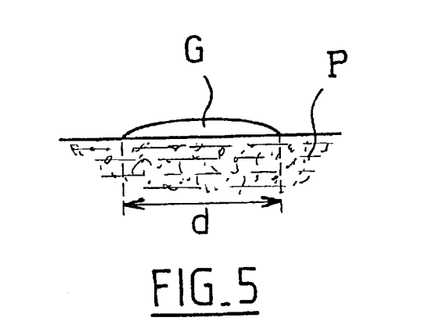
FIGS. 5 and 6 are diagrams showing the difference in contact area between the drop and the skin depending on the more or less greasy nature of the skin.
Figure 6:
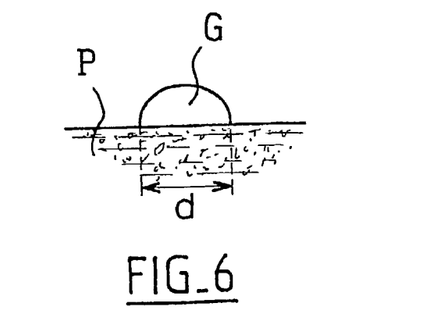

When the substance contained in the supply 12 is an aqueous substance, e.g., a solution of Erythrosin B in water, the contact area between the drop G and the skin differs depending on whether the skin is dry or greasy. With a greasy skin, the lipophilic and hydrophilic characteristics of the skin can be stronger. Thus, on the skin of the forehead, for example, the drop G tends to spread out more if the skin is very greasy, as shown in FIG. 5, whereas if the skin is moderately greasy, then the contact area is smaller, as shown in FIG. 6. It will thus be understood that by measuring the diameter d of the mark T (or some other length characterizing the extent of the mark T) left on the skin after the drop G has been removed, it is possible to obtain an indication concerning the more or less greasy nature of the skin.

By way of example, if a drop having a volume of about 20 μl of a solution of Erythrosin B in water at a concentration of 1 milligram per milliliter (mg/ml) is deposited on the top of the shoulder for a duration of about 1 minute, and the drop is then removed with a strip of blotting paper, the diameter of the mark is about 5 mm for skin which can be considered as being "normal," about 3 mm when the skin is "dry," and can be as much as about 7 mm when the skin is "greasy."

Figures 7, 8:
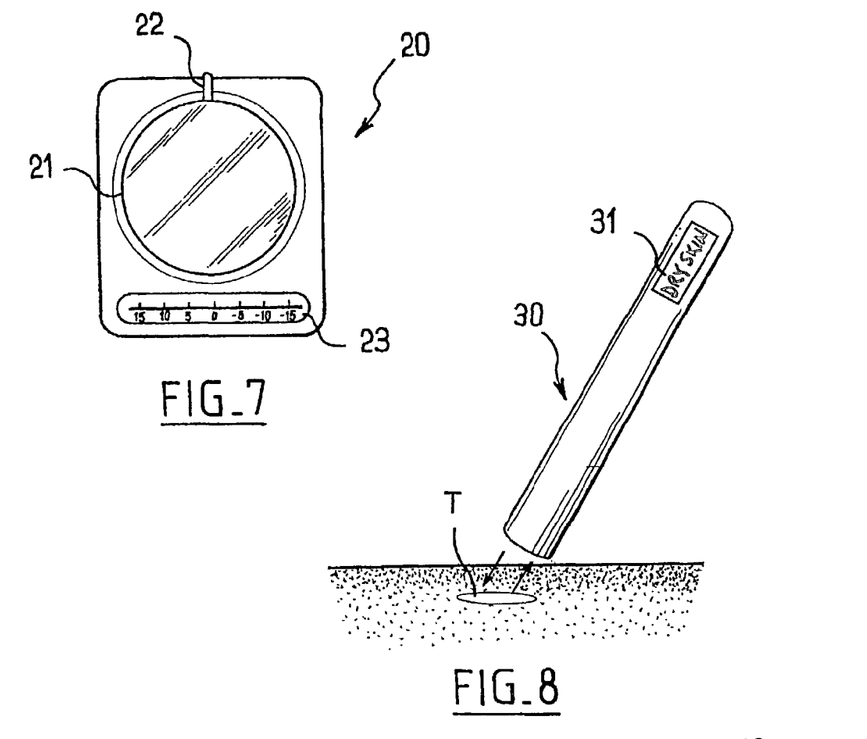
FIG. 7 shows another example of a device for applying a drop to the skin and for measuring the size of the resulting mark.
FIG. 8 is a diagram showing a device for measuring the size of a mark left on the skin by the drop of substance.

The invention is not limited to an embodiment of an applicator as shown in FIGS. 1 and 2. For example, another embodiment is shown in FIG. 7. As shown in this figure, an applicator 20 includes a supply 21 in the form, for example, of two flexible sheets assembled together around their periphery, e.g., by heat-sealing. The supply 21 communicates with a duct 22 formed between the two sheets. The free end of the duct can be cut off, torn away, pierced, or merely open when the user presses on the supply 21.

The applicator 20 can also serve as a medium for carrying a scale 23. The scale 23 can be a stick-on scale, which can be peeled off its backing so as to be applied to the skin beside the mark formed by the drop of substance deposited on the skin, in order to evaluate the size of the mark.

The invention is not limited to measuring the dimensions on a mark left by the drop on the skin using a scale that is placed beside the mark. In particular, it is possible to use other devices for evaluating the dimensions of the mark, e.g., a measuring device 30 as shown in FIG. 8. Such a device 30 can be in the form of a pen and configured to optically measure the mark. The device 30 can include a display 31 for providing information relating to the skin type.

Once the dimension of the mark has been measured, its dimensions (e.g., in mm) can be displayed directly in the display 31, or it can be converted into more elaborated information, for example, a score representing the more or less greasy nature of the skin or a non-numerical indication such as, for example, "greasy skin," "normal skin," or "dry skin."

In another embodiment, the invention includes a camera, e.g., a Webcam type camera, for measuring the size of the mark by observing the skin from a predetermined distance, possibly after placing an element of known dimensions beside the mark. The number of pixels can correspond to the mark being transformed into information representative of the dimensions of the mark.

The measurement device can deliver information relating to the size of the mark or to the type of skin directly or it can transmit information, possibly without displaying it, to a remote processing and display device. The information can be transmitted by wire or by wireless. For example, an interface can be provided between the device which takes the measurement and the device which processes the result of the measurement, such as a personal computer or a remote server.

Figure 9:
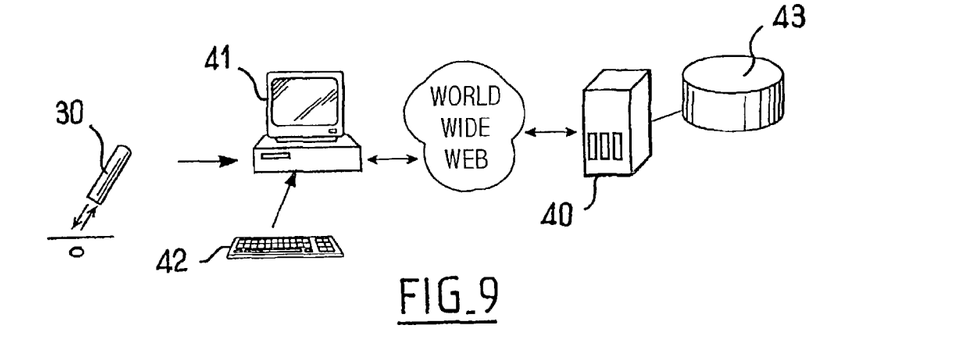
FIG. 9 represents an information system for collecting information and for transmitting the information to a remote server.

By way of example, FIG. 9 is a diagram showing a personal computer 41 connected via the Internet to a remote server 40. The personal computer 41 can receive information relating to the size of the mark left on the skin. This information can be input with a keyboard 42, for example, or transmitted by the measuring device 30 shown in FIG. 8, for example.

Figure 10:
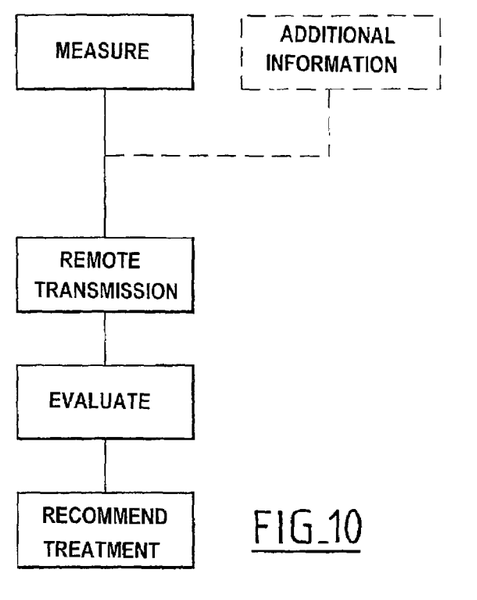
FIGS. 10 to 12 are flow charts illustrating various implementations of the invention.

By way of example, the remote server 40 can be programmed to determine skin type and to recommend care, as a function of the result of the measurement, and optionally as a function of additional information such as, for example, the age, the sex, the skin color of the person being examined. This process is represented by the flow chart of FIG. 10. The additional information may be input, for example, by answering a questionnaire that is displayed on the screen of the computer 41. Where appropriate, the results of the measurement, possibly as a function of optional additional information, can be evaluated by making use of information contained in a database 43 connected to the server 40.

Figure 11:
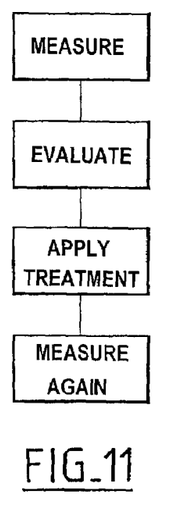
Figures 15, 17:
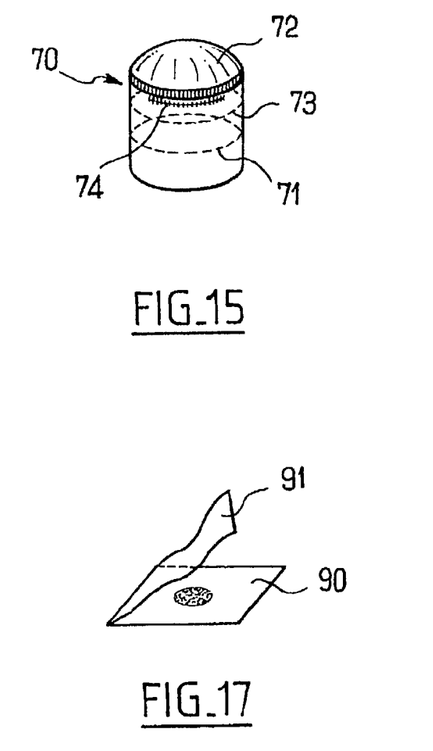
FIG. 15 is a diagram showing a scale associated with an optical system.
FIG. 17 is a diagram of a medium configured to transfer a trace left on the skin by a drop of substance.

It is also possible, when using a suitable substance, to transfer a print of the trace left on the skin by the drop of substance onto a medium so that the size of the trace can be measured indirectly. By way of example, FIG. 17 shows a medium 90 having an adhesive face configured to cover in a removable protective film 91, for example. The adhesive face of the medium can be applied to the skin after the drop of substance has been removed. The size of the mark transferred onto the medium can then be measured by various devices, possibly using graduations present on the medium.

Where appropriate, the protective film can be folded down onto the adhesive face after the trace has been transferred, with the medium as a whole then being sent by mail to a diagnosis center. Successive measurements can be made of the size of the mark left on the skin by drops of substance applied thereto at different instants, for example in order to determine the effectiveness of a substance, e.g., a care product, as represented by the flow chart of FIG. 11.

In particular, it is possible to perform with a first measurements of the dimensions of the mark in order to determine skin type, then apply a care product seeking for example to reduce the secretion of sebum if the skin is found to be too greasy or to provide lipids if the skin is found to be dry, and then perform a second measurement. If the size of the mark, as found from the second measurement, corresponds to "normal" skin, then the substance that has been applied can be considered as being suitable for the skin. If the size of the mark corresponds to skin that is too greasy or too dry, the dosage of the substance can be modified or the substance can be changed.

Figure 12:
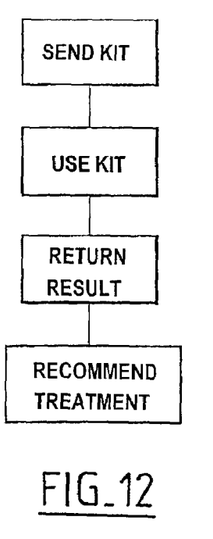

By way of example, skin can be evaluated in a beauty salon or it can be evaluated by the consumer herself. For example, a kit can be sent to a consumer for home use, and the result of the measurements can be sent to a diagnosis center in order to recommend care, as shown by the flow chart of FIG. 12. By way of example, the kit sent to a consumer can comprise an applicator together with a device for measuring the size of the mark left on the skin after the drop has been removed or has disappeared, possibly also with a strip of blotting paper or any other device enabling the drop to be removed. The kit can also include a medium making it possible by coming into contact with the skin to acquire an image of the trace left by the drop on the skin. The medium can also constitute a reply card, where appropriate.

Figure 13:
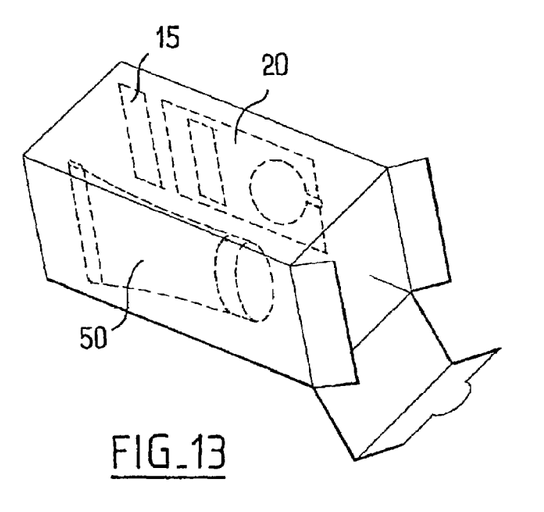
FIG. 13 shows a kit including a device for applying a drop of substance to the skin and for measuring the size of a mark left on the skin, and a care product.

As shown in FIG. 13, it is also possible to provide substance packaging, e.g., a cardboard box or a blister pack, with an applicator enabling a drop of colored substance to be applied to the skin, a device for removing the drop, and a device for measuring the dimensions of the mark left on the skin after the drop has been removed. The applicator can be, for example, the applicator shown in FIG. 7 and the device for removing the drop can be, for example, a strip of blotting paper 15. The box can also contain a container of substance 50 and a transfer medium, such as that shown in FIG. 17, for example.

Naturally, the invention is not limited to the examples given above. The substance applied to the skin can modify the optical properties of the skin not in the visible spectrum, but in the infrared or the ultraviolet, for example. Thus, the mark left on the skin after the drop has been removed can be observable only in the infrared or the ultraviolet, or it can become visible when illuminated with infrared or ultraviolet light. The mark can optionally be fluorescent, the substance used possibly containing Dansyl chloride, fluorescein, or rhodamine, for example.

It is also possible to apply to the skin a substance that is not colored but that colors the skin area exposed to the substance. The substance used can color the skin, e.g., by containing an oxidant capable of oxidizing in air, or an oxidizing agent (e.g., PPD and hydrogen peroxide). A reducing agent can also be used. It is also possible to use a substrate of an enzyme naturally present on the surface of the skin, e.g., glucose glucosidase and to use a developer to reveal the glucose that is released. It is also possible to use a polyphenol and then to use a polyphenol oxidase to reveal the size of the mark.

It is also possible to use any other substance suitable for modifying the physicochemical properties of the skin, for example a substance suitable for modifying properties other than color, e.g., the microrelief of the skin, or its electrical, capacitive, inductive, or magnetic properties. In these embodiments, a quantity related to the modified property is measured in order to evaluate the extent of the surface exposed to the substance. In order to modify the microrelief of the skin, it is possible for example to use an acid or a base. In order to modify the magnetic properties of the skin, the substance used can include magnetic particles, and in particular ferromagnetic particles.

The substance can also contain antibodies, in particular antibodies operative against keratins, having a ferromagnetic or chromophoric ligand grafted thereto. This can serve, for example, to improve fixing of the substance on the skin ready for subsequent development.

It is also possible to use a substance that leaves a trace on the skin which does not become apparent until the trace has been exposed to a developer. Thus, for example, it is possible to use a substance having adhesive properties, and to use as the developer a powder which is dusted onto the skin after the drop has been removed. The powder can adhere more strongly to the skin over the area that has been in contact with the drop of the adhesive substance, thus showing up the mark having dimensions which can be measured. The use of an adhesive substance may also serve to transfer a trace of adhesive onto a medium, where it can likewise be revealed with of a powder, for example. The use of an adhesive substance can also serve, where appropriate, when the skin is brought into contact with a transferable coating carried by a medium, to reveal the mark of the substance by transferring the coating onto the skin.

It is also possible to use a substance made with a solvent other than water, for example an alcoholic solvent or a lipidic solvent (e.g., glycerol, idooctane, iodomethane, octanol), e.g., as a function of the nature of the coloring agent.

Figure 14:
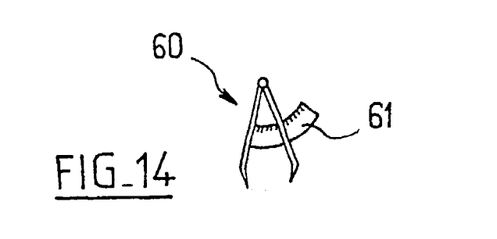
FIG. 14 is a diagram of a pair of dividers for measuring the size of a mark.

It is also possible to use other devices for measuring the size of the mark, for example a pick-glass (for counting threads) or a pair of dividers. FIG. 14 shows an example of a pair of dividers. In this figure, a pair of dividers 60 is shown carrying a scale 61 for measuring the angular spacing between its legs. The scale 61 may have non-numerical indications, e.g., directly giving skin type. Where appropriate, the scale may be associated with an optical system so as to form a device similar to a pick-glass.

By way of example, FIG. 15 shows a device 70 including two lenses 71 and 72 and a transparent intermediate element 73 having a scale 74 etched or printed thereon. The scale lies in the object focal plane of the lens 72 and in the image focal plane of the lens 71, for example, thereby enabling the observer to see an enlarged image of the mark together with the scale.

In the examples above, the scale can include a graduation, e.g., it may be graduated in millimeters. The user can then transform the measured value into information concerning skin type, using a correspondence table, for example. The scale can also have indications enabling skin type to be determined directly.

Figure 16:
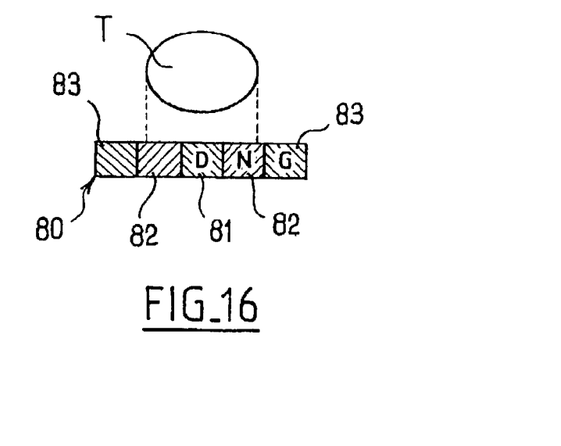
FIG. 16 is a diagram showing a scale carrying indications giving information directly about skin type, and shows how it is used.

By way of example, FIG. 16 shows a scale 80 meeting the above definition. The scale 80 has various regions in different colors, namely a central region 81 of a first color and of an extent that corresponds to dry skin, two middle zones 82 on either side of the central region and of an extent that corresponds to normal skin, and two extreme regions 83 of an extent corresponding to greasy skin. Letters or other inscriptions can be associated with the various regions in order to show what they correspond to, for example, the letters "N", "G", and "D."

To use the scale 80, the user places it beside the mark T, and determines which regions of the scale are in register with the mark T, the central region being placed over the center of the scale. In the example shown, the mark T corresponds to normal skin, since the mark T extends only as far as the middle regions 82.

Figure 18:
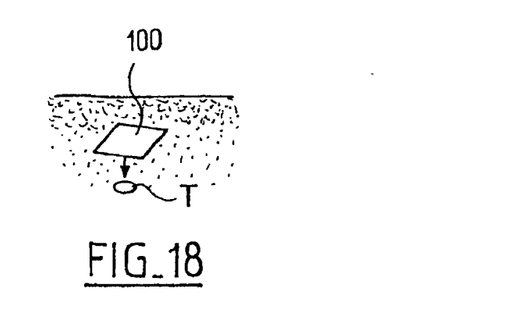
FIG. 18 is a diagram of a non-optical sensor.

It is also possible to use a non-optical sensor 100, as shown in FIG. 18. The non-optical sensor can include, for example, a juxtaposition of individual detector cells, which can be, for example, capacitive, resistive, or heat-sensitive. Sensors of this type are sold by the supplier SGS Thomson Micro Electronics under the trademark TOUCH CHIP™. The non-optical sensor 100 can serve to acquire an image of the microrelief of the skin. In a variant, the non-optical sensor 100 can enable an image to be acquired of a trace left on the skin by a substance that presents magnetic properties.

It is also possible to use a non-optical sensor integrated in a portable telephone, for example, such a sensor normally being used to identify the proprietor of the telephone. The telephone can store or download a program enabling the non-optical sensor to be used to determine the extent of the skin surface that has been exposed to a drop of a substance that is selected to leave, when removed, a trace that is detectable by the non-optical sensor.

In the embodiments of the invention described with reference to FIGS. 1 to 18, a drop of substance is applied to the zone of the skin whose type is to be determined, for example the shoulder, the forehead, or the forearm. It does not go beyond the scope of the present invention for the drop of substance to be applied to a collector member that has previously been put into contact with a zone of the skin so as to transfer sebum that might be present on the zone of the skin onto the collector member. The above description made with reference to FIGS. 1 to 18 applies equally to the case where the substance is applied to the collector member.

Figure 19:
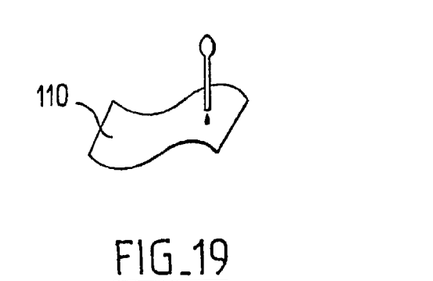
FIG. 19 shows an example of a collector member.

By way of example, the collector member can include a sheet 110 as shown in FIG. 19. Such a sheet can be based on cellulose fibers, for example. It can be passed over a zone of the skin that is rich in sebum, such as the forehead for example, and then a drop of substance can be deposited on the sheet, and the extent of the area of the sheet that comes into contact with the substance can be measured in the same manner as described above. Where appropriate, the sheet can carry graduations or a predetermined scale.

Figure 20:
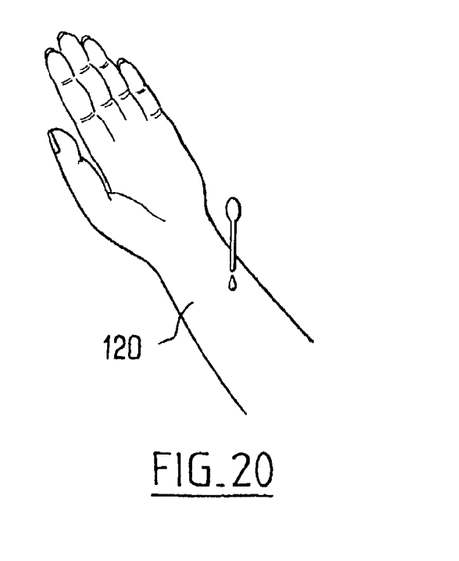
FIG. 20 shows another example of a collector member.

The collector member can also be a part of the human body, for example the forearm 120 as shown in FIG. 20. The forearm can be passed over the forehead in a first step so as to pick up sebum present on the forehead, and then a drop of substance can be deposited thereon so as to enable the extent of the area of skin that comes into contact with the substance to be evaluated. Where appropriate, a drop of substance can be deposited on the other forearm and the results of the evaluations can be compared.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A method of determining a skin type, comprising:
   applying at least one drop of substance onto a zone of skin or onto a collector member previously put into contact with said zone of skin, the substance being capable of modifying at least one physicochemical property of a surface of said zone or of said collector member exposed to said substance;
   after said at least one drop has disappeared or been removed, evaluating an extent of said surface exposed to said substance; and
   determining said skin type as a function of said extent.

2. A method according to claim 1, wherein said substance is a colored substance or a substance capable of coloring the skin or the collector member.

3. A method according to claim 2, wherein the substance is colored and includes a coloring agent in a solvent.

4. A method according to claim 3, wherein said coloring agent comprises at least one of Erythrosine B, carmine indigo, potassium permanganate, tannins, oxidation products of polyphenols, melanines, henna, anthocyanes, fluorescent substances, and Dansyl chloride.

5. A method according to claim 1, wherein the substance has magnetic properties.

6. A method according to claim 5, wherein the substance includes magnetic particles.

7. A method according to claim 6, wherein the substance includes particles containing iron.

8. A method according to claim 1, wherein the substance includes at least one antibody.

9. A method according to claim 8, wherein the antibody is specific to keratins.

10. A method according to claim 8, wherein said antibody is associated with one of magnetic particles, fluorescent compounds, enzymes, and an "ELISA" type system.

11. A method according to claim 1, wherein the substance is capable of modifying the microrelief of said zone of the skin or of the collector member.

12. A method according to claim 1, wherein a volume of the drop of substance applied to the skin or on the collector member is in a range of 5 µl to 100 µl.

13. A method according to claim 12, wherein said volume is in a range of 10 µl to 60 µl.

14. A method according to claim 1, comprising the step of removing the drop with an absorbent element.

15. A method according to claim 1, wherein the substance is colored or capable of coloring the skin or the collector member, and wherein the step of evaluating said extent is performed with one of a pair of dividers, a camera, a light ray, and a graduated scale.

16. A method according to claim 1, further comprising transmitting a result of an evaluation of an extend of said surface to a computer.

17. A method according to claim 16, wherein said step of transmitting is performed by mail or by computer network.

18. A method according to claim 17, wherein said step of transmitting is performed over the Internet.

19. A method according to claim 1, further comprising a step of recommending care based on said determining step.

20. A method according to claim 1, wherein said step of evaluating said extent is performed in situ.

21. A method according to claim 1, further comprising the step of transferring a trace left on said zone of the skin or on the collector member by said drop of substance, and wherein said evaluating step is performed after said transferring step.

22. A method according to claim 1, wherein said applying step is performed by directly applying the drop of substance onto said zone of the skin.

23. A method according to claim 1, wherein said applying step is performed by applying the drop of substance onto said collector member previously put into contact with said zone of the skin.

24. A method according to claim 23, wherein the collector member is a portion of a human body.

25. A method according to claim 24, wherein said portion of the human body is a forearm.

26. A method according to claim 24, further comprising comparing results of a first evaluation on the collector member prior to transferring sebum from said zone of the skin onto the collector member, and a second evaluation performed after said transferring of sebum.

27. A method according to claim 25, further comprising comparing results of an evaluation performed on one forearm after said forearm has been passed over a forehead with results of another evaluation performed on another forearm.

28. A method according to claim 23, wherein the collector member is a medium independent of a human body.

29. A method according to claim 28, wherein said medium is a sheet.

30. A method of treating skin, the method comprising:
applying at least one drop of a test substance on a zone of said skin or on a collector member which was previously in contact with said zone, wherein the test substance modifies at least one physicochemical property of a surface of said zone of skin or of the collector member exposed to said test substance;
after the drop has disappeared or been removed, evaluating an extent of said surface which was in contact with said drop;
determining a skin type as a function of said extent; and
treating the skin as a function of said skin type.

31. A method according to claim 30, wherein said substance is colored or capable of producing coloring on said zone of the skin or on the collector member.

32. A method according to claim 30, wherein the applying step is performed by applying the drop of test substance to a forearm, and said treating step is performed by treating body portions in addition to said forearm.

33. A method according to claim 30, wherein the applying step is performed by applying the drop of the test substance to a forehead, and said treating step is performed by treating a face including said forehead.

34. A method of determining treatment effectiveness, the method comprising:
applying at least one drop of substance to a zone of the skin or to a collector member previously in contact with said zone, the substance being capable of modifying at least one physicochemical property of a surface of said zone of skin or of the collector member in contact with said drop;
evaluating an extent of said surface which was in contact with said drop, after the drop has been removed or has disappeared, by observing modifications induced by said substance;
performing a treatment on said skin;
repeating the steps of applying and evaluating;
comparing results before and after said treatment; and
deducing an indication concerning the effectiveness of the treatment based on said comparing step.

35. A method of evaluating physiological age of skin, the method comprising:
applying at least one drop of substance onto a zone of skin or onto a collector member previously in contact with said zone, the substance being capable of modifying at least one physicochemical property of a surface of said zone of skin or of the collector member exposed to said substance;
after the drop has disappeared or been removed, evaluating an extent of said surface which was in contact with said drop by observing modifications induced by said substance; and
determining the age of the skin as a function of said extent.

36. An assembly comprising:
an applicator adapted to apply a drop of a substance to the skin or to a collector member, the substance being capable of modifying at least one physicochemical property of a surface of the skin or of a collector member exposed to said substance, and
at least one measuring device configured to measure a length of said surface which was in contact with said drop, and to display a skin type as a function of a result of the measurement after said drop has disappeared or been removed.

37. An assembly according to claim 36, wherein said measuring device is a scale.

38. An assembly according to claim 36, wherein the applicator comprises a supply of substance and an end portion.

39. An assembly according to claim 38, wherein said end portion opens when the supply is pressed.

40. An assembly according to claim 38, wherein said end portion can be snapped off by a user.

41. An assembly according to claim 38, wherein said end portion can be cut off by a user.

42. An assembly according to claim 38, wherein said end portion can be punctured by a user.

43. An assembly according to claim 37, wherein said scale is carried by the applicator.

44. An assembly according to claim 37, wherein said scale is a stick-on scale.

45. An assembly according to claim 37, wherein said scale includes markings which indicate skin type directly.

46. An assembly according to claim 36, wherein the applicator has a supply of substance formed in contact with at least one flexible wall.

47. An assembly according to claim 46, wherein said supply of substance is formed between two superposed sheets.

48. An assembly according to claim 36, wherein the applicator comprises a duct through which the drop is delivered, the inside diameter of the duct being in a range of 50 μm to 3 mm.

49. An assembly according to claim 48, wherein said inside diameter is in a range of about 0.1 mm to about 2 mm.

50. An assembly according to claim 36, wherein the measuring device comprises a camera.

51. An assembly according to claim 36, wherein the measuring device comprises at least one magnetic sensor.

52. An assembly according to claim 36, wherein the measuring device comprises at least one non-optical sensor which delivers an image of a microrelief of the skin.

53. An assembly according to claim 36, wherein the measuring device comprises an interface which transfers data to at least one of a personal computer and a computer network.

54. A kit comprising the assembly according to claim 36, further comprising a container of said substance.

55. A kit according to claim 54, wherein said substance is a skin care product.

56. A device for determining a skin type, said device comprising:
  means for measuring an extent of a surface having at least one physicochemical property modified compared with a zone situated around said surface, and
  means for displaying a skin type as a function of the extent measured with said means for measuring.

57. A device according to claim 56, wherein said means for displaying comprises means for displaying information in non-numerical form.

58. A device according to claim 57, wherein said means for displaying displays at least one of "dry skin," "normal skin," and "greasy skin."

59. A system for identifying a skin type, said system comprising:
  a substance to apply on a zone of skin and capable of modifying at least one physicochemical property of a surface of said zone exposed to said substance, and
  a scale comprising:
    a support;
    a marking on said support, said marking indicating directly said skin type, as a function of a measured dimension of a mark resulting from an application of at least one drop of the substance onto the zone of skin,
    said scale being configured to be viewed simultaneously with the mark when said marking indicates said skin type.

60. A system for identifying a skin type, said system comprising:
  a substance to apply on a zone of skin or into a sebum collector member and capable of modifying at least one physicochemical property of a surface of said zone exposed to said substance,
  a scale comprising:
    a support;
    a marking on said support, said marking indicating directly said skin type, as a function of a measured dimension of a mark resulting from an application of at least one drop of the substance onto the zone of skin or into the sebum collector member, and
    an optical system enabling the scale to be viewed simultaneously with an enlarged image of a mark on a skin.

61. A system according to claim 59, further comprising a pair of dividers coupled to said scale.

62. A method of determining skin type comprising:
  applying a drop of a substance on a surface having skin sebum;
  leaving said substance in contact with said surface long enough for said substance to change a property of said surface;
  measuring a quantity characterizing a contact area between said substance and said surface to evaluate an extent of said surface exposed to said substance; and
  identifying said skin type based on said evaluated extent of said surface.

63. A system for identifying a skin type, said system comprising:
  a substance to apply on a zone of skin and capable of modifying at least one physicochemical property of a surface of said zone exposed to said substance,
  a scale comprising:
    a support;
    a marking on said support, said marking indicating directly said skin type, as a function of a non-electronically measured dimension of a mark resulting from an application of at least one drop of the substance onto the zone of skin.

64. An assembly comprising:
  an applicator adapted to apply a drop of a substance to the skin or to a collector member, the substance being capable of modifying at least one physicochemical property of a surface of the skin or of a collector member exposed to said substance; and
  at least one measuring device for evaluating an extent of said surface which was in contact with said drop, after said drop has disappeared or been removed,
  wherein said measuring device comprises at least one magnetic sensor.

65. An assembly comprising:
  an applicator adapted to apply a drop of a substance to the skin or to a collector member, the substance being capable of modifying at least one physicochemical property of a surface of the skin or of a collector member exposed to said substance; and
  at least one measuring device for evaluating an extent of said surface which was in contact with said drop, after said drop has disappeared or been removed,
  wherein said measuring device comprises at least one non-optical sensor which delivers an image of a microrelief of the skin.

66. A system according to claim 60, wherein the substance is configured to apply to a zone of skin, and said marking is configured to indicate directly said skin type as a function of a measured dimension of a mark resulting from application of the at least one drop of the substance onto the zone of skin.

* * * * *

UNITED STATES PATENT AND TRADEMARK OFFICE
CERTIFICATE OF CORRECTION

PATENT NO.        : 7,211,043 B2                                       Page 1 of 1
APPLICATION NO. : 10/289344
DATED             : May 1, 2007
INVENTOR(S)       : Francis Pruche et al.

It is certified that error appears in the above-identified patent and that said Letters Patent is hereby corrected as shown below:

On The Title page, Item (75) Inventors, change "Rubinstein" to --Rubinstenn--.

Signed and Sealed this

Thirtieth Day of October, 2007

JON W. DUDAS
*Director of the United States Patent and Trademark Office*